United States Patent [19]

Sanz-Moncasi et al.

[11] Patent Number: 5,536,641
[45] Date of Patent: Jul. 16, 1996

[54] MONOCLONAL ANTIBODY SPECIFIC FOR VASCULAR ENDOTHELIAL CELL ANTIGEN ENDOGLYX-1 AND USES THEREOF FOR DETECTION OF, AND ISOLATION OF, VASCULAR ENDOTHELIAL CELLS

[75] Inventors: Maria P. Sanz-Moncasi, Zaragoza, Spain; Pilar Garin-Chesa, Biberach, Germany; Elisabeth Stockert; Lloyd J. Old, both of New York, N.Y.; Wolfgang J. Rettig, Biberach, Germany

[73] Assignee: Memorial Sloane Kittering Cancer Center, New York, N.Y.

[21] Appl. No.: 243,288

[22] Filed: May 17, 1994

[51] Int. Cl.$^6$ .............................. G01N 33/53; C12N 5/20; C07K 16/28
[52] U.S. Cl. ...................... 435/7.21; 435/240.27; 435/70.21; 435/172.2; 435/723; 435/261; 530/388.2; 530/388.22
[58] Field of Search ................ 530/388.22, 388.2, 530/413; 435/240.27, 7.21, 7.23, 172.2, 70.21, 261; 436/548

[56] References Cited

FOREIGN PATENT DOCUMENTS 9411023  5/1994  WIPO .

OTHER PUBLICATIONS

Rettig et al., "Identification of endosialin, a cell surface glycoprotein of vascular endothelial cells in human cancer", Proc. Natl. Acad. Sci. USA 89: 10832–10836 (11–92).

Schlingemann et al., "Differential Expression of Markers for Endothelial Cells, Pericytes and Basal Lamina in the Microvasculature of Tumors and Granulation Tissue", Amer. J. Path. 138(6): 1335–1347 (1991).

Garin–Chesa et al., "Cell surface glycoprotein of reactive stromal fibroblasts as a potential antibody target in human epithelial cancers", Proc. Natl. Acad. Sci. USA 87: 7235–7239 (Sep. 1990).

Ruiter et al., "Monoclonal Antibody–Defined Human Endothelial Antigens as Vascular Markers", J. Invest. Derm. 93(2) (supp): 255–32S (Aug. 1989).

Goerdt et al., Exp. Cell Biol., 57:185–192, 1989.

Primary Examiner—Paula K. Hutzell
Attorney, Agent, or Firm—Felfe & Lynch

[57] ABSTRACT

An antigen which is specific to vascular endothelium is described. Described is a cell surface antigen which consists of four subunits, of 190, 145, 125 and 110 kd as determined by SDS-PAGE under reducing conditions as is a monoclonal antibody specific to this antigen. Uses, both diagnostic and therapeutic, are also described.

14 Claims, 7 Drawing Sheets

MONOCLONAL ANTIBODY SPECIFIC FOR VASCULAR ENDOTHELIAL CELL ANTIGEN ENDOGLYX-1 AND USES THEREOF FOR DETECTION OF, AND ISOLATION OF, VASCULAR ENDOTHELIAL CELLS

This application is based upon work supported, in part, by a grant from the National Cancer Institute (CA-57486). The U.S. government may have certain rights in the invention.

FIELD OF THE INVENTION

This invention relates to the study of the surface of vascular endothelial cells. More particularly, it relates to the characterization of a surface antigen specific to vascular endothelial cells, a monoclonal antibody which specifically binds to the antigen, and a hybridoma which produce the monoclonal antibody. The antigen, referred to hereafter as endoGlyx-1, is a cell surface glycoprotein consisting of four subunits. More details of the antigen are provided in the application which follows. Also described are various uses for the monoclonal antibody, such as diagnostic and therapeutic agents, as well as for the antigen itself, as, e.g., an immunogen.

BACKGROUND AND PRIOR ART

Interest in surface antigens of vascular endothelial cells has come from several lines of research, including studies of lymphocyte homing, inflammation, blood clotting, and tumor metastasis. Exemplary of the vast body of literature in this area are Bevilacqua, Ann. Rev. Immunol. 11:767–804 (1993); Shimizu et al., Immunol. Today 13:106–112 (1992); Zimmerman et al., Immunol. Today 13:93–99 (1993); Butcher et al., Cell 67:1033–1037 (1991); Schlingemann et al., Lab. Invest. 52:71–76 (1985); Schlingemann et al., Am. J. Pathol. 138:1335–1347 (1991); Picker et al., Ann. Rev. Immunol. 10:561–591 (1992); Asborn, Cell 62:3–6 (1990); Roth, Immunol. Today 13:100–105 (1992); Weidner et al., New Eng. J. Med. 324:1–8 (1991). Throughout these studies, monoclonal antibodies (mAbs) have proven to be valuable tools for dissecting the antigenic structure of endothelial cells in different organs, tissues or segments of the vascular system, and the endothelial responses to inflammation, tissue damage, and tumor growth. Furthermore, mAbs have been used in the biochemical and molecular genetic characterization of endothelial antigens and in the functional analyses of endothelial molecules in vitro and in vivo.

Several categories of endothelial antigens have been distinguished, based on their distribution patterns in normal and lesional blood vessels. These include (i) antigens with wide distribution in the vascular system, such as Factor VIII-related antigen (FVIIIRA), PAL-E, and CD13, as per Schlingemann et al., Lab Invest. 52:71–76 (1985); Kuzu et al., J. Clin. Path. 45:143–148 (1992); (ii) antigens restricted to vessels in specific organs or tissues, or to unique histologic types of vessels, as illustrated by vascular addressins and GlyCAM-1; and (iii) inducible antigens, such as E-selectin, VCAM-1, and ICAM-1, that are not present or expressed at low levels in normal endothelium but are upregulated in inflamed tissues in vivo and/or induced or cultured endothelial cells by proinflammatory cytokines, notably tumor necrosis factor (TNF) and interleukin-1 (IL-1) (Pober et al., Lab. Invest. 64:301–305 (1991); Kuzu et al., Lab. Invest. 69:322–328 (1993)).

However, none of the previously identified endothelial antigens serves as a unique endothelial cell lineage marker; i.e., they are either not widely expressed in the vascular system (antigenic heterogeneity) or they are expressed on certain nonendothelial cells. Time and again, when mAbs with apparent specificity for endothelium were subjected to rigorous specificity analyses, including tests with panels of cultured cells that represent diverse cell lineages, and immunohistochemical analysis of fetal and adult normal tissues and lesional tissues, unexpected reactivities and nonendothelial cells were uncovered. Bevilacqua, supra; Shimizu et al., supra; Zimmerman et al., supra; Butcher et al., supra, Kuzu et al., supra; Ruiter et al., J. Invest. Dermatol. 93:25–32 (1989); Gougos et al., Int. Immunol. 4:83–92 (1992); Alles et al., J. Histochem. Cytochem. 34:209–214 (1986). For example, FVIIIRA is present in megakaryocytes and platelets, and CD31, CD36, and CD34 are expressed by subsets of lymphocytes and myelomonocytic cells. Similarly, BW200 is expressed in mesothelium and glomerular epithelium, PAL-E is detected in the epidermis (Ruiter et al., supra); and endoglin is present in placental trophoblastic cells, hematopoietic precursors, and several other cell types (Gougos et al., supra).

A cell surface antigen specific to vascular endothelium, referred to as endoGlyx-1 hereafter, has now been identified. This molecule is a glycoprotein with four subunits, bound together by disulfide bonds. The molecule appears to have a molecular weight in excess of 500 kd on SDS-PAGE under non-reducing conditions. Its four subunits, under reducing conditions, appear to have molecular weights of about 190 kd, 140 kd, 125 kd, and 110 kd. The antigen is described herein, as is a monoclonal antibody which specifically binds to it. Also disclosed are various diagnostic and therapeutic uses for the monoclonal antibody and the antigen.

BRIEF DESCRIPTION OF THE FIGURES

FIG. 1 presents a number of panels showing immunohistochemical staining and detection of endoGlyx-1 in normal and malignant tissues.

FIG. 1A: newborn umbilical cord vein (endoGlyx-1$^+$);

FIG. 1B: normal adult breast (endoGlyx-1$^+$ capillaries);

DETAILED DESCRIPTION OF PREFERRED EMBODIMENTS

Example 1

Figure 1A:
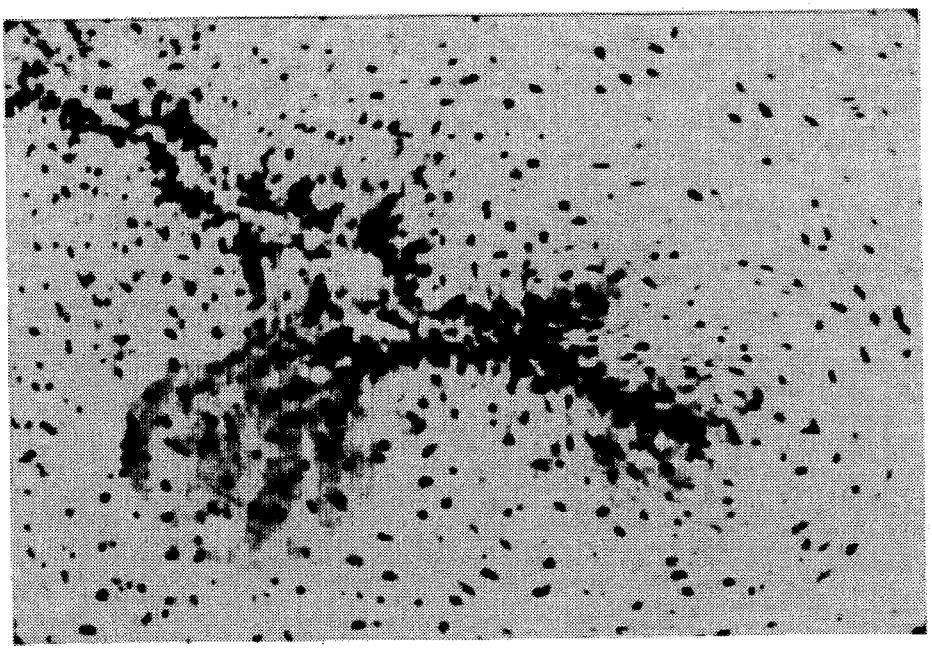
In FIGS. 1A and C–M, the magnification is ×25.

The first step of the study involved the preparation of monoclonal antibodies ("mAbs" hereafter), which bound, specifically, to endothelial cells.

BALB/C mice were immunized with cultured human umbilical vein endothelial cells ("HUVEC" hereafter). These cells are described by Jaffe et al., J. Clin. Invest. 52:2745–2753 (1973); Jaffe et al., J. Biol. Chem. 262:8557–8565 (1987); both of which are incorporated by reference in their entirety. The mice were immunized with $10^6$ cells which had been suspended in 100 ul of PBS. The first immunization was subcutaneous, followed by intraperitoneal immunization, also with $10^6$ cells. Two further immunizations were carried out, at four week intervals. Each immunization was performed subcutaneously, with $10^6$ cells in PBS. No adjuvant was used in any of the immunizations.

Spleens of the subject animals were removed, and separated into individual cells which were then fused to SP2/0 myeloma cells.

Following fusion and culturing, the culture supernatants from the hybridoma were tested for binding to a panel of cultured cell types. The panel consisted of HUVECs, EAhy 926 which is an HUVEC derived immortalized cell line (Edgell et al., Proc. Natl. Acad. Sci. USA 80:3734–3737 (1983)), fibroblasts, breast cancer cell line MCF-7, renal cancer cell line SK-RC-7, and melanoma cell line SK-MEL-28. The initial screening, described herein, was carried out using the mixed hemadsorption rosetting assay, as described by Rettig et al., J. Immunol. 183:4884–4489 (1987), incorporated by reference herein. Any supernatants which showed selective reactivity with HUVEC were selected for further analysis. Fifteen hybrid cultures were identified in this fashion, and these hybridomas were subcloned, using standard limiting dilution methods.

The fifteen cloned hybridoma cells were then expanded in vitro, and the culture supernatants were tested for reactivity using a larger panel of cultured cell lines. Supernatant from one clone, i.e., H572, was found to contain a monoclonal antibody which bound exclusively with HUVECs. The mAb was unreactive with cultured fibroblast, sarcoma, neuroblastoma, melanoma, glioma and carcinoma cells. It was also unreactive with cells taken from peripheral blood and bone marrow, including lymphocytes, granulocytes, monocytes, megakaryotyces, platelets, and erythrocytes. Table 1 sets forth the results. The mAb, while reactive with HUVECs, was unreactive with cultured cells of mesenchymal, neuroectodermal, and epithelial derivation. "FACS" analysis of peripheral blood cells, and immunocytochemical analysis of nucleated bone cells showed that H572 is unreactive with normal lymphoid and hematopoietic cells. Again, the assay employed was that of Rettig et al., supra.

TABLE 1

Cell surface reactivity of mAb H572 with short-term cultures of normal human cells, established tumor cell lines, and normal, uncultured peripheral blood and bone marrow cells

| Cell type | Designation | mAb H572 (titer$^{-1}$) |
|---|---|---|
| Cultured cells: | | |
| HUVEC (n = 12) | | 1,250–6,250 |
| Fibroblast | GM05387, WI-38, Hs27, F135-35-18 | — |
| Sarcoma | SW872, TE-85, SAOS-2 | — |
| Neuroblastoma | LA-N-1, SK-N-SH, SMS-MSN | — |
| Melanoma | SK-MEL-13, SK-MEL-28, SK-MEL-31 | — |
| Glioma | SK-MG-12, SK-MG-26, U251MG | — |
| Carcinoma | MCF-7, MDA-MB468, SK-RC-28 HT-29, DLD-1, SK-OV-6 | — |
| Peripheral blood and bone marrow: | | |
| Lymphocytes | | — |
| Granulocytes | | — |
| Monocytes | | — |
| Megakaryocytes, platelets | | — |
| Erythrocytes | | — |

Example 2

H572 was then tested for in vivo reactivity with tissues, in immuno-histochemical assays. Tissue samples were obtained either from autopsy or surgical specimens. These samples were embedded in OCT, frozen in isopentane which had been precooled with liquid nitrogen, and stored at −70° C. The tissues were tested using the well known avidin-biotin immunoperoxidase method, as described by Garin-Chesa et al., J. Histochem. Cytochem. 36:383–389 (1988), the disclosure of which is incorporated by reference in its entirety, but is outlined herein. Briefly, five micron thick frozen sections were cut, mounted on poly-(L-lysine)-coated slides, air-dried, and fixed in acetone (4° C., ten minutes). The sections were treated with 0.3% $H_2O_2$ for three minutes to block endogenous peroxidase, followed by blocking with normal horse or goat serum for 30 minutes, at room temperature.

Figure 1B:
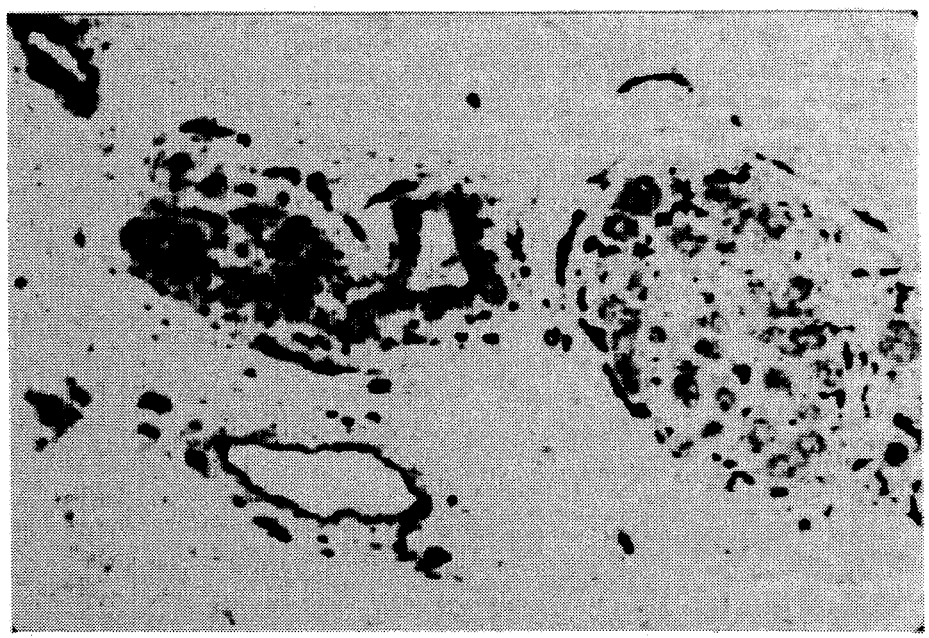
in FIG. 1B it is 12.5. Specifically.

The slides were incubated at 4° C., with mAbs (hybridoma culture supernatant, dilution of 1:2; or purified Ig, 5–20 ug/ml), rabbit anti-FVIIIRA (diluted 1:120,000), or negative control antibodies, for 12–18 hours. Sections were washed, and incubated with biotinylated horse anti-mouse or goat anti-rabbit Ig, for 30 minutes at room temperature, followed by avidin-biotin horseradish peroxidase complex (1:100 dilution, at 1:1 ratio). Final reaction product was visualized with the chromogen 3,3'diaminobenzidine. Sections were then counterstained with hematoxylin. This extensive analysis included umbilical cord, skin, mammary gland, lung, esophagus, stomach, small and large intestine, liver, pancreas, thyroid gland, adrenal gland, kidney, urinary bladder, prostate, testis, ovary, fallopian tube, uterus, smooth and skeletal muscle, thymus, spleen, and lymph node tissues. The mAb was found to react exclusively with vascular endothelial cells. Exemplary of the staining pattern with normal cells are FIGS. 1A and 1B. EndoGlyx-1 expression was found in capillaries, veins, arterioles, and muscular arteries. Staining was consistent with uniform cell surface and cytoplastic distribution of the antigen, with some accentuation of the abluminal side of endothelial cells in some vessels, as per FIG. 1A.

Organ specific patterns of endoGlyx-1 expression were observed. In the liver, endothelial cells of vessels in portal spaces were positive, central veins were weakly positive, and sinusoids were negative. In the spleen, trabecular veins and arteries, and central arterioles of the white pulp were positive, but sinusoidal endothelial cells of highly vascularized red pulp of the spleen were negative. In lymph nodes, subcapsular sinus endothelial cells, afferent and efferent blood vessels showed immunoreactivity.

In lungs, all vessels showed expression, including alveolar capillaries.

In kidney tissues, endoGlyx-1 staining was seen in glomerular tufts, with variable staining intensity, and in peritubular capillaries, and larger arterial and venous vessels.

Example 3

Figure 1C:
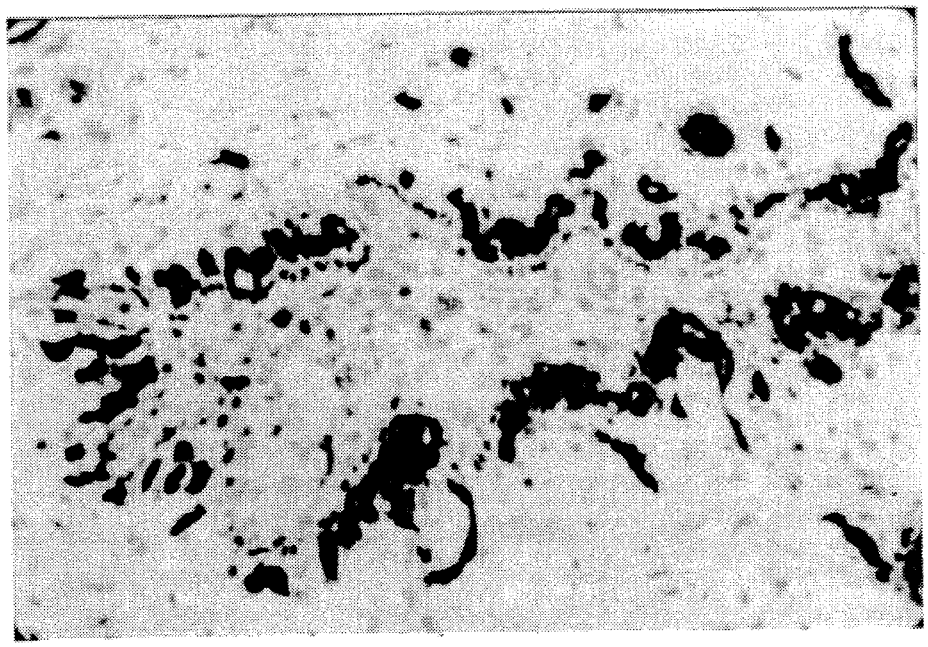
FIG. 1C: breast carcinoma (abundant endoGlyx-1$^+$ capillaries surrounding a tumor cluster)
Figure 1D:
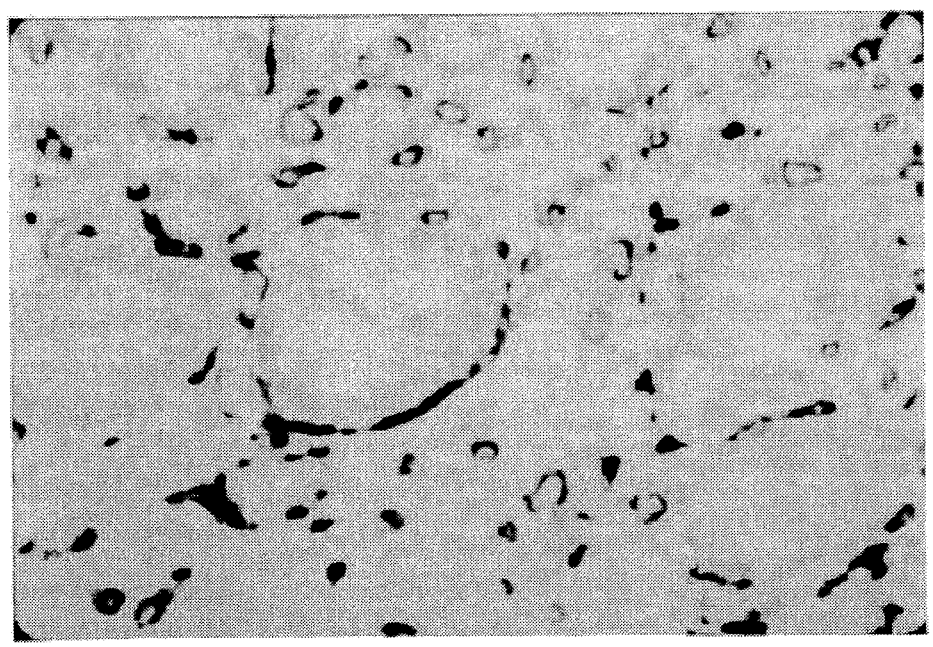
FIG. 1D: 16 week fetal kidney (endoGlyx-1$^+$ endothelial cells)
Figure 1E:
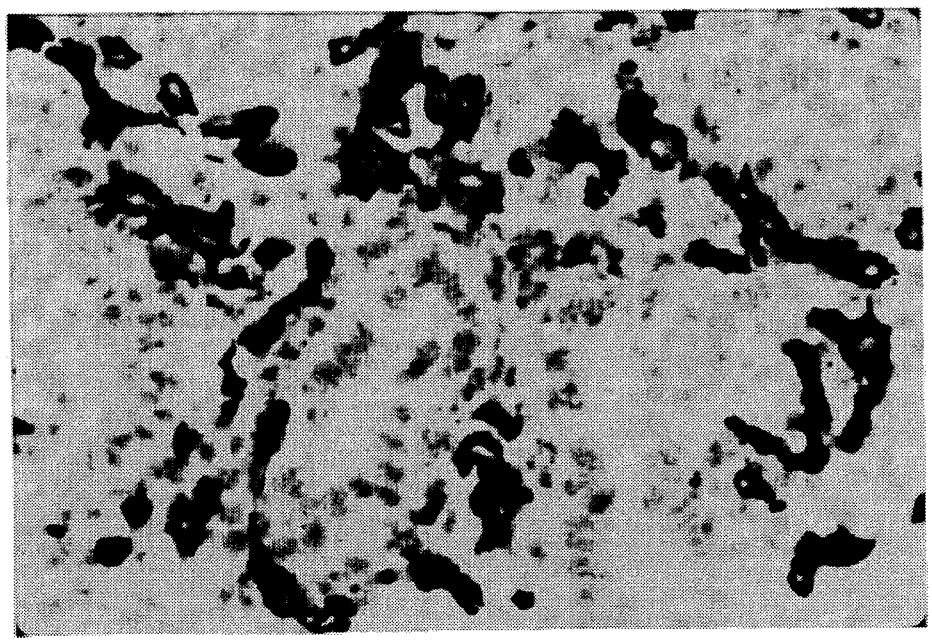
FIG. 1E: 16 week fetal lung (endoGlyx-1$^+$ endothelial cells)
Figure 1F:
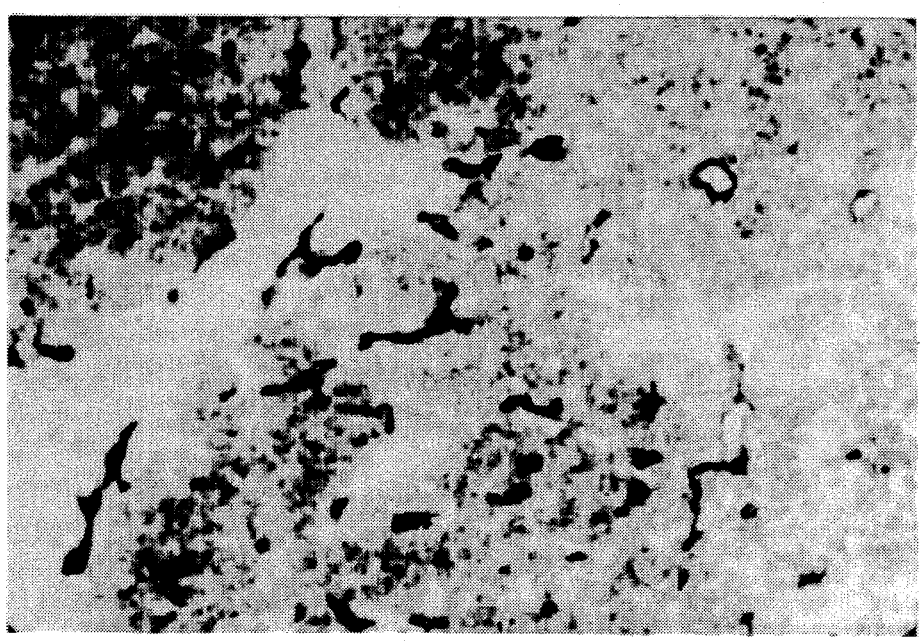
FIG. 1F: fetal thymus (16 weeks), (endoGlyx-1$^+$ endothelial cells)

Normal tissues of a 16 week old fetus were also available for the study, including skin, connective tissue with primitive cartilage formation, thymus, spleen, pancreas, liver, stomach, ovary, lung, kidney, heart, cerebral cortex and cerebellum. The assay was the same as above. In each tissue, strong endoGlyx-1 immunostaining of the vascular endothelium was observed, with the exception of liver and splenic sinusoids. FIGS. 1D, 1E and 1F present the staining patterns observed in fetal, lung, fetal kidney, and fetal thymus. No other cell types present showed any endoGlyx-1 staining.

Example 4

Figure 1G:
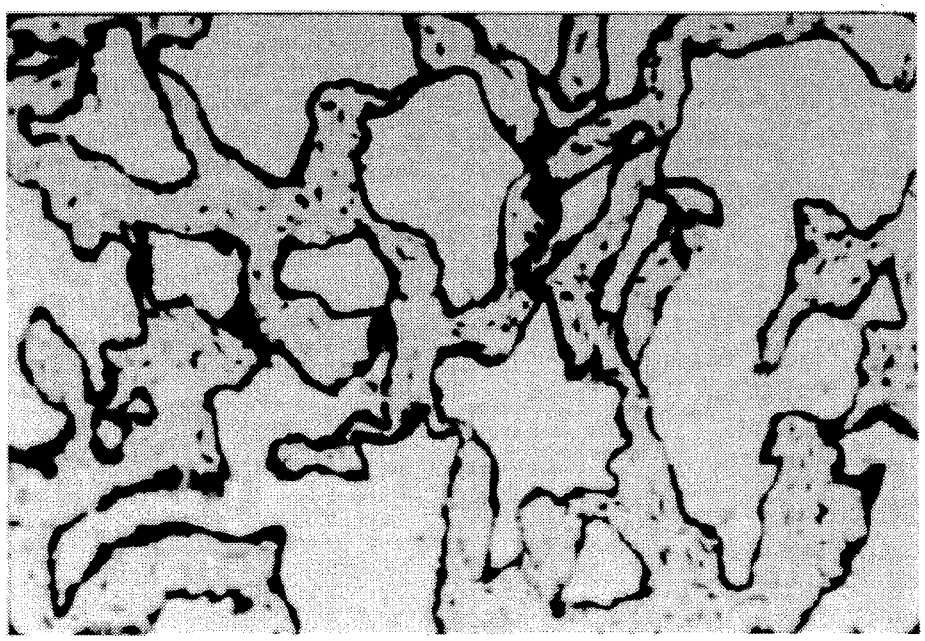
FIG. 1G: Hemangioma with endoGlyx-1$^+$ endothelial cells.
Figure 1H:
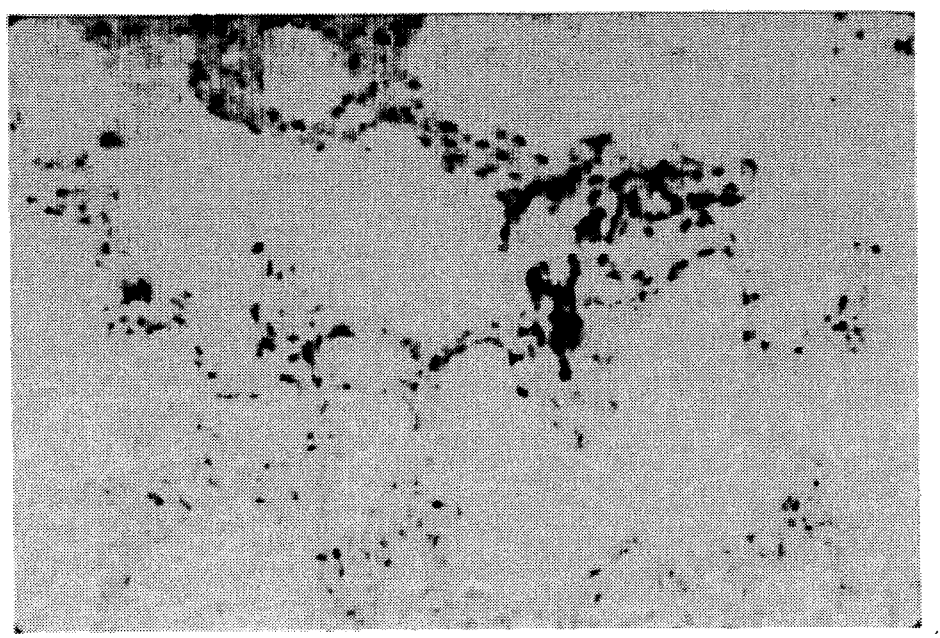
FIG. 1H: Hemangioma of 1G, stained with mAb PAL-E, showing only focal immunostaining.
Figure 1J:
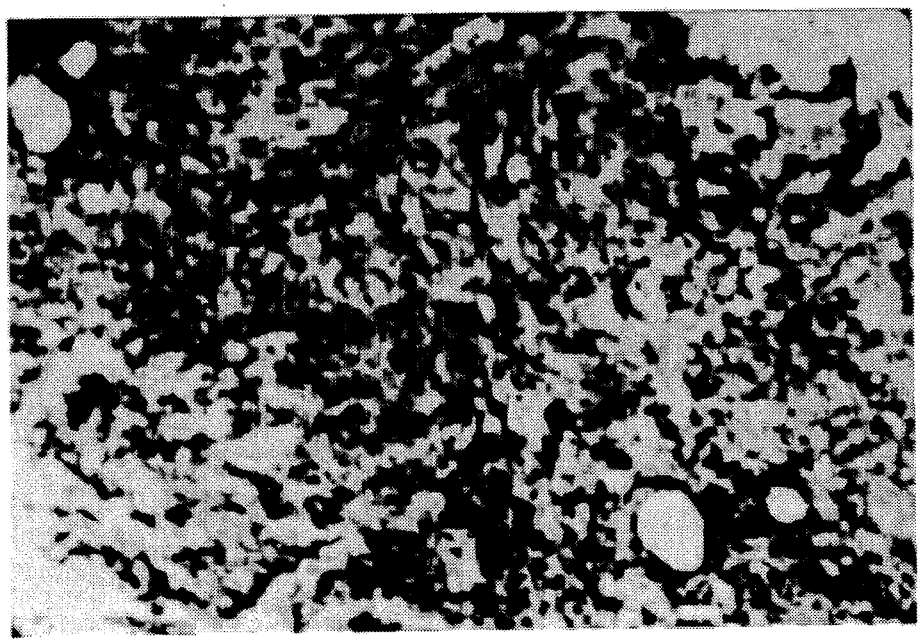
FIG. 1J: Angiosarcoma with endoGlyx-1$^+$ neoplastic cells.

The same assay was carried out in vascular neoplasms. Table 2 summarizes the results. Some hemangiomas and angiosarcomas retained expression of EndoGlyx-1 (FIGS. 1G and 1J), while neoplastic cells of hemangiopericytomas were consistently endoGlyx-1 negative, which is in keeping with their derivation from pericytes rather than vascular endothelial cells. In contrast, nontransformed, capillary endothelial cells in the stroma of hemangiomas showed expected endoGlyx-1 staining.

Example 5

Figure 1K:
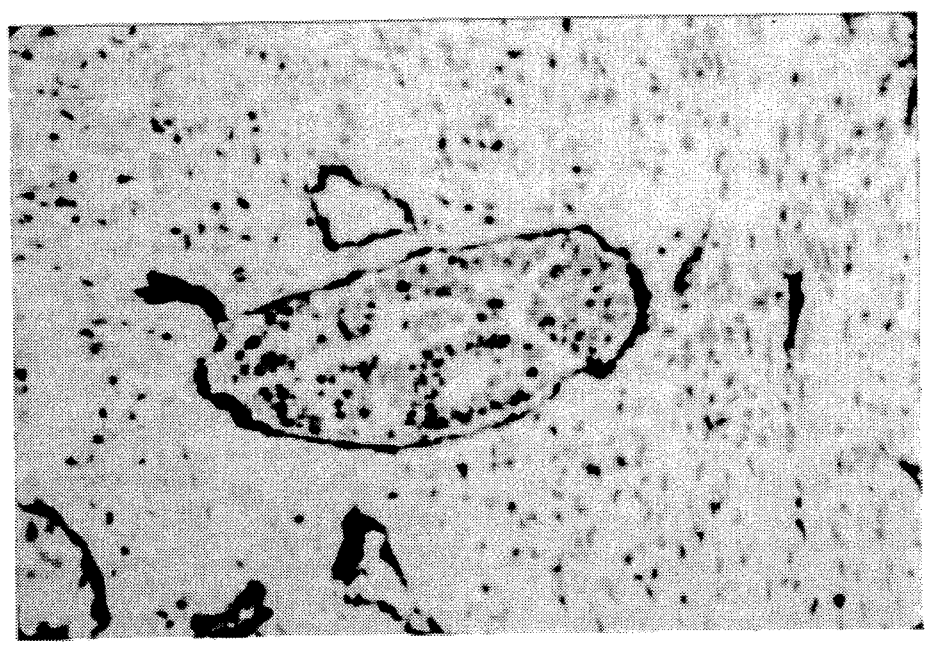
FIG. 1K: Ovarian cancer with tumor cells in an endoGlyx-1$^+$ blood vessel.

Extended analysis with mAb H572 of endoGlyx-1 expression in tumor blood vessels of over 100 neoplasms of diverse histological types, also summarized in Table 2, showed consistent antigen expression in stromal blood vessels of carcinomas, sarcomas, lymphoid, and neuroectodermal neoplasms. Exemplary are the staining patterns of FIGS. 1C and 1K, breast and ovarian cancer, respectively.

TABLE 2

Endoglyx-1 expression in human tumor tissues determined by the avidin-biotin immunoperoxidase method

| | | H572 immunoreactivity | | |
|---|---|---|---|---|
| Tumor type | N | Tumor cells | Stromal fibroblasts | Tumor vascular endothelium |
| Vascular tumors | | | | |
| Hemangioma | 3 | + | − | NE |
| Angiosarcoma | 2 | + | − | NE |
| Hemangiopericytoma | 8 | − | − | + (8/8) |
| Other tumor types | | | | |
| Carcinomas | 77 | − | − | + (77/77) |
| Sarcomas | 15 | − | − | + (15/15) |
| Neuroectodermal | 10 | − | − | + (10/10) |
| Lymphomas | 10 | − | − | + (10/10) |

+ = Antigen positive
− = Antigen negative
NE = not evaluatable, because of prominent immunostaining of tumor cells

Example 6

A comparative study was then carried out, where normal and lesional tissue were tested, side by side, with (i) mAb H572, (ii) rabbit anti-FVIII related antigen αCD31; and (iii) mAb PAL-E. The purpose was to compare specificity and sensitivity of these reagents in immunohistochemical identification of vascular endothelial cells.

Figure 1L:
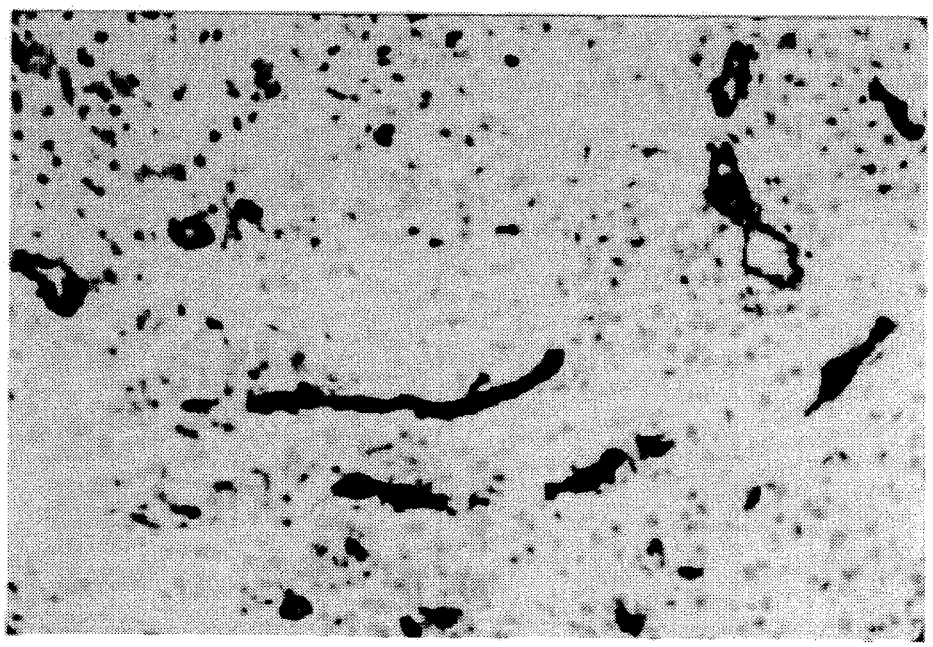
FIG. 1L: Osteoarthritis with endoGlyx-1$^+$ endothelial cells, and endoGlyx-1$^+$ inflammatory cells.
Figure 1M:
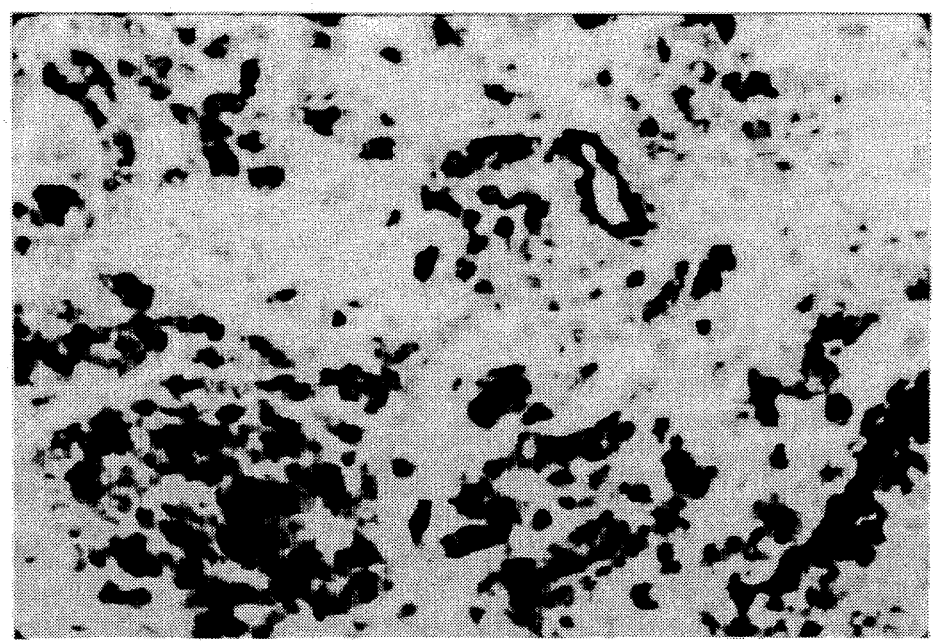
FIG. 1M: The osteoarthritis of 1L, stained with anti-α CD31, showing immunostaining of endothelial cells and infiltrating lymphocytes.

The analysis confirmed the previous reports of variable expression of FVIII related antigen αCD31 in normal and tumor blood vessels (Kuzu et al., J. Clin. Path. 45:143–148 (1992)). The comparison also found that the PAL-E antigen, αCD31 and endoGlyx- 1 are expressed widely in vascular beds of human solid neoplasms. The comparison of αCD31 distribution and endoGlyx-1, represented by FIGS. 1L (endoGlyx-1) and 1M (αCD31), shows sharp divergence. The mAbs against αCD31 tested, i.e., SG134 (Goyert et al., in McMichael et al., ed. Leukocyte Typing III. White Cell Differentiation Antigen (Oxford University Press, (1988), at 1049), and EA 195, react with endothelial cells and subsets of peripheral blood leukocytes, nucleated bone marrow cells, cells on the red pulp of the spleen, and lymphoid cells present in tumor and inflammatory tissues.

While the PAL-E antigen resembles αCD31 and endoGlyx-1 in its widespread distribution on endothelial cells, it was expressed at very low levels or was undetectable in some muscular arteries and arterioles which showed strong αCD31 and endoGlyx-1 immunostaining. Also, in kidney tissue, the PAL-E antigen was present in peritubular capillaries but was absent from glomerular tufts and arterioles. Unlike αCD31 or endoGlyx-1, immunostaining of the PAL-E antigen was observed in basal keratinocytes of normal epidermis, as was reported by Ruiter et al., J. Invest. Dermatol 93:25–32 (1989). These results differ from the report of Leenstra et al., Cancer 72(1): 3061–3067 (Nov. 15, 1993), wherein it was reported that the PAL-E antigen was found on tumor pillories, and not on normal brain capillary pillories. EndoGlyx-1 was found on both types of cells, however, showing a distinct difference in distribution. Side by side analysis of several hemangiomas for endoGlyx-1 and expression of the PAL-E antigen identified some lesions uniformly positive for endoGlyx-1 expression but largely negative for the PAL-E antigen. In the latter cases, immunostaining was restricted to capillary endothelial cells in the hemangioma stroma, which will be seen by comparing FIGS. 1G and 1H.

Example 7

Radio-immunoprecipitation assays were carried out with mAb H572.

Cultures of HUVECs were radiolabelled with a mixture of [$^{35}$S]methionine and [$^{35}$S]-cysteine (40 μCi/ml; 1 Ci=37GB1), or [$^3$H]glucosamine (40 μCi/ml), by culturing for 18–24 hours in the presence of these labels, following Rettig et al., Brain Res. 590:219–228 (1992), the disclosure of which is incorporated by reference. The cells were extracted in lysis buffer [0.01M Tris.HCl/0.15M NaCl/0.01M MgCl$_2$/0.5% Nonidet P-40/aprotinin (20 ug/ml)/2 mM phenylmethylsulfonyl fluoride] and then used for immunoprecipitation assays, following well known techniques, using either H572, or unrelated, negative control.

Any immunoprecipitates were then separated on 6% SDS-gels, under reducing conditions, and were detected by fluorography.

Figure 2B:
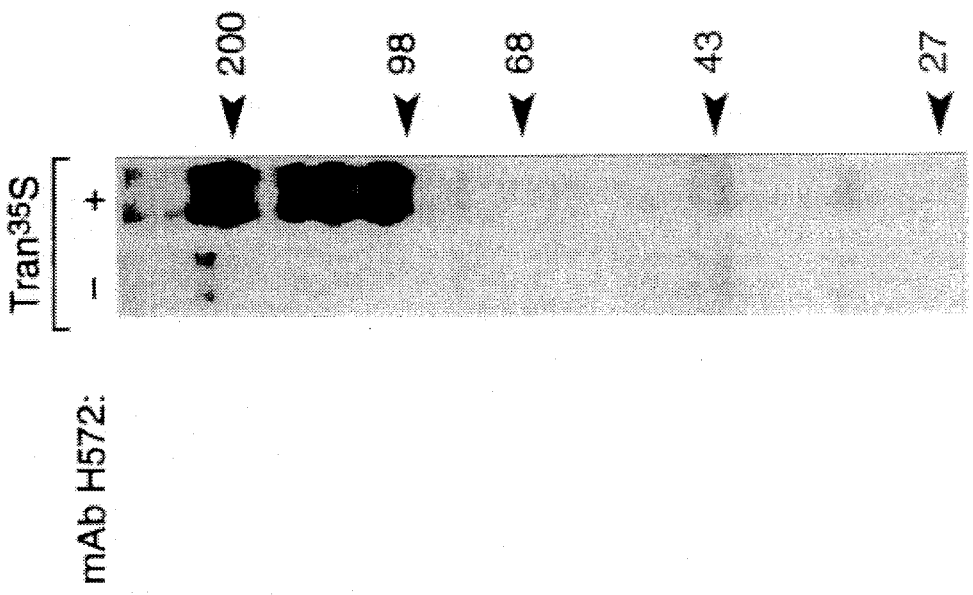
FIGS. 2A and 2B show the immunoprecipitation of endoGlyx-1 glycoproteins from NP40 extracts of [$^3$H] glucosamine (FIG. 2A), or Trans $^{35}$S (FIG. 2B) labelled HUVEC cultures. Lysates were tested with mAb H572 ("+"), or unrelated, negative control IgG1 ("−"). The immunoprecipitates were separated on 6% SDS-gels under reducing conditions, and were detected by fluorography.
Figure 2A:
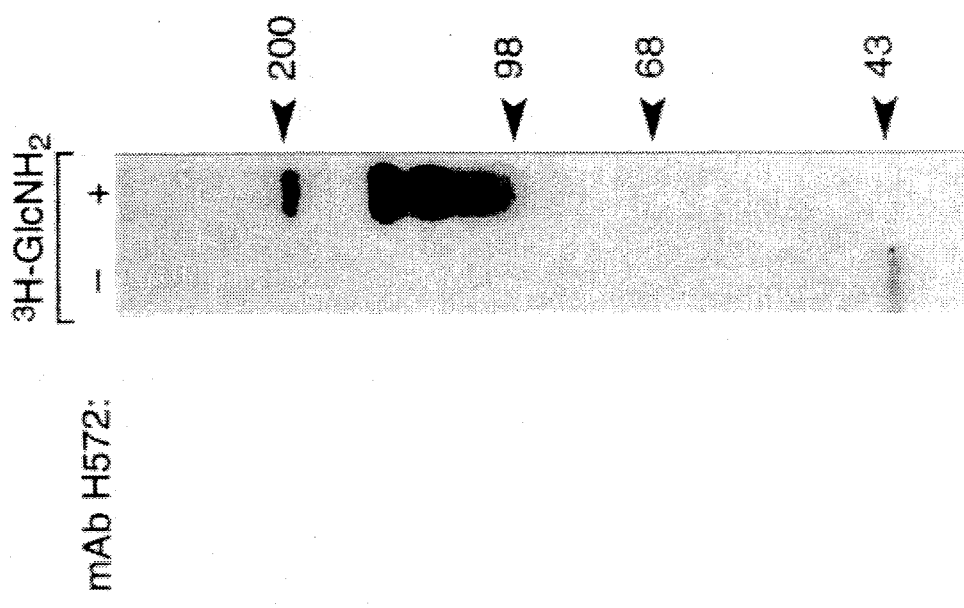

The results, presented in FIG. 2, show the mAb H572 precipitated several protein species. These migrated at Mr 190,000, 140,000, 125,000, and 110,000 on SDS-PAGE, using reducing conditions.

When the experiment was done using SDS-gels under non-reducing conditions, the immunoprecipitate barely entered the 7% SDS-running gel, thereby suggesting a molecular size of greater than 500,000 for a disulphide bonded complex.

Since the 190, 140 and 125 kd subunits—and—to a lesser extent, the 110 kd subunit are all seen after [$^3$H]glucosamine labelling, the subunits are glycoproteins.

The molecule will be referred to as "endoGlyx-1" hereafter.

Example 8

An experiment was carried out to determine if endoGlyx-1 expression is modulated by inflammatory cytokines. In metabolic labelling experiments using Trans $^{35}$S label, following example 7, supra, HUVECs which were cultured in the presence of TNFα (50 ng/ml), IL-1β (2 ng/ml), or TGF-β1 (2 ng/ml), did not show changes in abundance or subunit composition of the molecule.

The foregoing disclosure teaches a methodology for production of monoclonal antibodies such as H572, which specifically bind to an antigen characteristic of vascular endothelial cells. The antigen is a glycoprotein, with four subunits, having molecular weights of about 190 kd, 140 kd, 125 kd, and 110 kd as determined by SDS-PAGE, under reducing conditions. Under non-reducing conditions, tile antigenic complex exhibits a molecular weight greater than about 500 kd, as determined by SDS-PAGE.

Monoclonal antibodies which specifically bind to vascular endothelial cell specific antigens, such as the endoGlyx-1 molecule discussed supra, and hybridomas which produce them, are also described. Exemplary of these monoclonal antibodies is H572. A hybridoma cell line which produces H572 has been deposited at the American Type Culture Collection, 12301 Parklawn Drive, Rockville, Md., under Accession Number HB 11608, on Apr. 7, 1994, in accordance with the Budapest Treaty. This mAb is of the IgG1 subclass, although those of ordinary skill in the art will understand that the antibody class and subclass may differ in other mAbs which bind to the same target.

It is to be understood that "monoclonal antibody" as the term is used herein embraces not only the products of hybridomas, but also monoclonal antibodies produced via other well known methodologies. Such methodologies include, but are not limited to, e.g., the use of cells which have been "immortalized" by transfection with Epstein Barr Virus or other immortalizing agents. Also embraced are monoclonal antibodies produced via genetic engineering, such as by transformation of appropriate host prokaryotic or eukaryotic cells. Also covered are chimeric antibodies. These are well known in the art as antibodies which contain portions of antibodies from two or more species. For example, it is well known to produce chimeric antibodies which contain the CDR region of a murine monoclonal antibody, and the remaining portions of a human monoclonal antibody. Such chimeras are extremely useful, e.g., in a therapeutic context. It also embraces the well known binding fragments of antibodies, such as the Fab, F(ab)$_2$, Fv and other binding fragments. Also covered by the invention are oligomeric, and polymeric constructions, where a plurality of monoclonal antibodies of the recited specificity are complexed to each other.

The antibodies of the invention can clearly be used in diagnostic methods to identify the site of vascular endothelium or a vascular endothelium the cell, e.g., whereby the monoclonal antibody is contacted to a sample to be assayed, and its binding is monitored. Such binding can be determined using any of the standard immunoassay protocols known to the artisan, including, but not being limited to, radioimmunoassays, enzyme linked immunosorbent assays, sandwich assays, competitive assays, chromophoric assays and so forth. Many of these assays require the use of a detectable label which is attached to the antibody, and any of the labels known to the art, including radioactive, chromophoric, and fluorophoric substrates, enzymes, magnetic particles, and metallic particles may be used. In carrying out the assays, the sample of interest may be, e.g., a tissue sample or body fluid sample. Further, the specificity of the mAb permits the artisan to use it in vivo diagnosis. Among the varieties of in vivo diagnosis which can be used, radioimaging is particularly preferred.

Of particular value is the use of the mAbs of the invention in the identification of endothelial cell precursors, by using an mAb in a sample which is known to be free of endothelium cells. Binding of the antibody to target indicates the presence of an endothelial cell precursor. While the mAb can be used in any biological sample, such as tissue samples and body fluid samples, it is especially useful in the assaying of bone marrow and peripheral blood, where endothelial cell precursors may be found.

The ability of the monoclonal antibodies of the invention to target vascular endothelium makes them particularly useful in a therapeutic context.

Normal vascular endothelial cells do not generally proliferate in a healthy individual, in contrast to the proliferation observed in tumor associated vascular endothelium. By linking the monoclonal antibody of the invention to a cell proliferation-inhibiting agent, one can inhibit or retard tumor proliferation. The agent does not affect those endothelial cells which are not proliferating, so there is no problem with the complex of proliferation inhibitor/monoclonal antibody adversely affecting other cells. This therapy comprises administering an amount of the monoclonal antibodies of the invention sufficient to inhibit proliferation of the endothelial cells targeted, thereby preventing angiogenesis in lesional tissue, as well as sparing other proliferating cells, such as bone marrow, which do not express the targeted antigen, i.e., EndoGlyx-1. In addition, the mAbs may be used in connection with liposomal delivery systems, where the liposome contains the inhibiting or other therapeutic agent, and the mAbs target these to the site of the vascular cells.

Such targeting can also be used in directed gene therapy. This approach, carried out in vitro, e.g., complexes the mAbs of the invention to a nucleic acid molecule which codes for a protein of interest, or a complex which contains the nucleic acid molecule. The nucleic acid molecule may be carried by a liposome or other agent. As the mAb is targeted to the endothelial cells, there is every reason to expect that the gene or nucleic acid molecule of interest will also "target" the endothelial cell.

The monoclonals, either alone or with the various materials described supra, may be formulated in various reagent formats. For example, the mAb can be combined with a pharmacologically acceptable carrier. When used in connection with the various materials disclosed herein, these can be attached to the mAb to form a conjugate, the conjugate then being combined with a pharmacologically acceptable carrier. It is also possible to prepare a kit type of reagent, wherein the mAb and the second substance are presented in separate portions, both of which are included in a container means. Such reagents are useful both therapeutically and diagnostically.

Also envisioned and within the scope of the invention is the isolation of both the coding region for EndoGlyx-1 and the regulatory elements which control its expression. These elements are of particular interest, in view of endoGlyx-1's exclusive expression by vascular endothelial cells. It is expected that such regulatory elements may be operably linked to genes of interest and then transfected into endothelial cells. Such transfection will lead to expression of the protein of interest in endothelial cells only.

It has been mentioned, supra, that the mAbs of the invention are useful diagnostically, in that various labels may be attached to the mAb, with the labelled material then being used to target and/or identify endothelial cells. The ability to bind specifically to these cells also places the ability to isolate or to purify endothelial cells in the hands of the skilled artisan. The basic methodology essentially involves contacting the mAbs of the invention to a sample containing the target vascular endothelial cell. The mAb has been treated in some way which makes it removable from the sample. For example, the mAb can be conjugated to a solid phase, such as a column or a microbead. The mAb binds to the targeted cell, and the resulting complex is removed from the sample. The thus removed cells can be treated in various ways. Genes can be inserted, and the transformants cultured for transfer back into the subject. The removed cells can also be simply cultured without transformation, so as to provide adequate supplies of the cells if and when necessary.

The isolated glycoprotein endoGlyx-1 of the invention can be used as an immunogen, either alone or in combination with a suitable adjuvant. It can also be used in studies to determine its amino acid sequence, which in turns leads to the preparation of probes for isolating the nucleic acid molecule which codes for the protein of the antigen.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A monoclonal antibody which specifically binds to a glycoprotein antigen expressed by vascular endothelial cells, wherein said glycoprotein antigen is that which is specifically recognized by monoclonal antibody H572 produced by the hybridoma deposited under the accession number ATCC HB 11608 and consists of four subunits, said subunits having molecular weights of 190,000, 140,000, 125,000 and 110,000 daltons as determined by SDS-PAGE under reducing conditions.

2. The monoclonal antibody of claim 1, designated mAb H572 and produced by the hybridoma deposited under the accession number ATCC HB 11608.

3. The monoclonal antibody of claim 1, wherein said monoclonal antibody is a murine/human chimeric antibody.

4. The monoclonal antibody of claim 3, wherein said chimeric antibody consists of murine CDR regions, and the remainder of said antibody is a human antibody.

5. An antigen binding fragment of the monoclonal antibody of claim 1.

6. The antigen binding fragment of claim 5, selected from the group consisting of an Fab, $F(ab)_2$, or $F_v$ fragment.

7. A hybridoma cell line which produces the monoclonal antibody of claim 1.

8. Hybridoma H572, deposited under the accession number ATCC HB 11608.

9. Method for identifying a vascular endothelium cell comprising contacting a sample with the monoclonal antibody of claim 1, and detecting binding of said monoclonal antibody wherein binding of said monoclonal antibody is indicative of the presence of a vascular endothelial cell in said sample.

10. The method of claim 9 wherein said monoclonal antibody is labelled.

11. The method of claim 10, wherein said monoclonal antibody is labelled with a radioactive label, a chromophoric label, or a fluorophoric label, an enzyme, a magnetic particle or a metal particle.

12. The method of claim 9, wherein said sample is a tissue sample.

13. The method of claim 9, wherein said sample is a body fluid sample.

14. Method for separating a vascular endothelial cell from a sample containing said cell, comprising contacting said sample with the monoclonal antibody of claim 1 conjugated to a solid phase under conditions which allow a monoclonal antibody-target cell complex to form and removing the resulting complex from said sample.

* * * * *

UNITED STATES PATENT AND TRADEMARK OFFICE
CERTIFICATE OF CORRECTION

PATENT NO. : 5,536,641

DATED : July 16, 1996

INVENTOR(S) : Sanz-Moncasi et al.

It is certified that error appears in the above-identified patent and that said Letters Patent is hereby corrected as shown below:

On the title page, item [73]:

line 1, change "Sloane Kittering" to --Sloan Kettering--.

In column 4, line 13, change "megakaryotyces" to --megakaryocytes--.

In column 6, line 2, change "Endoglyx-1" to -- EndoGlyx-1 --.

In column 7, line 16, after "]" add -- , --.

In column 7, line 53, change "tile" to --the--.

In column 9, line 1, change "EndoGlyx-1" to -- endoGlyx-1 --.

In column 9, line 28, change "EndoGlyx-1" to -- endoGlyx-1 --.

Signed and Sealed this

Twentieth Day of July, 1999

Attest:

Q. TODD DICKINSON

Attesting Officer

Acting Commissioner of Patents and Trademarks